(12) United States Patent
Lee et al.

(10) Patent No.: US 9,295,413 B2
(45) Date of Patent: Mar. 29, 2016

(54) FITNESS MONITOR

(71) Applicant: Garmin Switzerland GmbH, Schaffhausen (CH)

(72) Inventors: Wai C. Lee, Overland Park, KS (US); Michael K. George, Edgerton, KS (US); Andrew J. Skarsgard, Cochrane (CA)

(73) Assignee: Garmin Switzerland GmbH (CH)

( * ) Notice: Subject to any disclaimer, the term of this patent is extended or adjusted under 35 U.S.C. 154(b) by 103 days.

(21) Appl. No.: 14/024,353

(22) Filed: Sep. 11, 2013

(65) Prior Publication Data

US 2014/0200691 A1    Jul. 17, 2014

Related U.S. Application Data

(60) Provisional application No. 61/753,747, filed on Jan. 17, 2013, provisional application No. 61/868,880, filed on Aug. 22, 2013.

(51) Int. Cl.
| | |
|---|---|
| *G06F 19/00* | (2011.01) |
| *A61B 5/11* | (2006.01) |
| *A61B 5/00* | (2006.01) |

(52) U.S. Cl.
CPC .............. *A61B 5/1118* (2013.01); *A61B 5/4866* (2013.01); *A61B 5/681* (2013.01)

(58) Field of Classification Search
CPC ..... A61B 5/681; A61B 5/1118; A61B 5/4866
See application file for complete search history.

(56) References Cited

U.S. PATENT DOCUMENTS

| | | | |
|---|---|---|---|
| 5,976,083 A | 11/1999 | Richardson et al. | 600/300 |
| 6,145,389 A | 11/2000 | Ebeling et al. | 73/865.4 |
| 6,301,964 B1 | 10/2001 | Fyfe et al. | 73/510 |
| 6,513,532 B2 | 2/2003 | Mault et al. | 128/921 |
| 7,261,690 B2 | 8/2007 | Teller et al. | 600/300 |
| 7,690,556 B1 | 4/2010 | Kahn et al. | 235/105 |

(Continued)

FOREIGN PATENT DOCUMENTS

JP    2008-142258    6/2008

OTHER PUBLICATIONS

Fitbit Zip: http://www.pcmag.com/article2/0,2817,2410013,00.asp; published prior to Sep. 11, 2013.

(Continued)

*Primary Examiner* — James S McClellan
*Assistant Examiner* — Kevin Carter
(74) *Attorney, Agent, or Firm* — Samuel M. Korte; Maxwell M. Ali

(57) ABSTRACT

A fitness monitor comprises a housing, a wrist band, a motion sensor, a display, a non-transitory memory element and a processing element. The wrist band is coupled to the housing and configured to attach to a wrist of a user. The motion sensor is configured to sense motion of the user and generate motion data. The display is coupled to the housing and configured to present information associated with user activity. The memory element is located in the housing and configured to store the activity data and a daily activity goal. The processing element is operably coupled to the memory element and configured to determine daily activity data, a daily activity goal corresponding to a predetermined level of activity for the user, compute an activity countdown and level of inactivity, and present, on the display, the activity countdown and inactivity indicia indicating the level of inactivity.

20 Claims, 4 Drawing Sheets

(56) References Cited

U.S. PATENT DOCUMENTS

| | | | | |
|---|---|---|---|---|
| 8,311,769 | B2 | 11/2012 | Yuen et al. | 702/160 |
| 8,360,936 | B2 | 1/2013 | DiBenedetto et al. | 482/8 |
| 8,827,815 | B2* | 9/2014 | Burroughs et al. | 463/42 |
| 2001/0049470 | A1 | 12/2001 | Mault et al. | 600/300 |
| 2004/0116837 | A1 | 6/2004 | Yamaguchi et al. | 600/595 |
| 2005/0272564 | A1* | 12/2005 | Pyles et al. | 482/54 |
| 2006/0020177 | A1 | 1/2006 | Seo et al. | 600/300 |
| 2006/0052727 | A1 | 3/2006 | Palestrant | 600/595 |
| 2008/0150731 | A1 | 6/2008 | Laukkanen et al. | 340/573.1 |
| 2008/0319353 | A1 | 12/2008 | Howell et al. | 600/595 |
| 2009/0043531 | A1 | 2/2009 | Kahn et al. | 702/149 |
| 2010/0331145 | A1* | 12/2010 | Lakovic | G04F 10/00 482/8 |
| 2011/0098928 | A1* | 4/2011 | Hoffman | A63B 24/0062 702/5 |
| 2012/0084053 | A1* | 4/2012 | Yuen et al. | 702/160 |
| 2012/0253485 | A1* | 10/2012 | Weast | G06F 19/3481 700/91 |
| 2012/0274508 | A1* | 11/2012 | Brown | G04F 10/00 342/357.25 |
| 2013/0184613 | A1 | 7/2013 | Homsi et al. | 600/595 |
| 2014/0085077 | A1* | 3/2014 | Luna et al. | 340/539.11 |
| 2014/0200691 | A1* | 7/2014 | Lee et al. | 700/91 |

OTHER PUBLICATIONS

Fitbit: http://www.fitbit.com/zip/specs; published prior to Sep. 11, 2013.

Fitbit Flex: http://reviews.cnet.com/wearable-tech/fitbit-flex-black/4505-34900_7-35566773.htm; published prior to Sep. 11, 2013.|.

Fitbit Ultra: http://www.pcmag.com/article2/0,2817.2395762,00.asp; published prior to Sep. 11, 2013.

Nike FuelBand: http://reviews.cnet.com/wearable-tech/nike-fuelband/4505-34900_7-3516558.html; published prior to Sep. 11, 2013.

Fitbit One: http://www.pcmag.com/article2/0,2817.2411271,00.asp; published prior to Sep. 11, 2013.

Nike SportBand: http://www.pcmag.com/article2/0,2817,2351558,00.asp; published prior to Sep. 11, 2013.

Jawbone Up: http://www.pcmag.com/article2/0,2817,2413303,00.asp; published prior to Sep. 11, 2013.

Lark Life: http://www.pcmag.com/article2/0,2817,2413317,00.asp; published prior to Sep. 11, 2013.

Misfit Shine: http://www.pcmag.com/article2/0,2817,2423341,00.asp; published prior to Sep. 11, 2013.

Amiigo: http://www.forbes.com/sites/jasonevangelho/2013/01/31/wearable-fitness-tech-amiigo-bracelet-detects-detailed-activity-now-available-for-pre-order/; published prior to Sep. 11, 2013.

Smart Health LifeTrak: http://smarthealthusa.com/c200/; published prior to Sep. 11, 2013.

Polar Loop: http://www.polarloop.com/; published prior to Sep. 11, 2013.

International Search Report and Written Opinion from corresponding PCT/US2013/073141, filed Dec. 4, 2013.

* cited by examiner

FITNESS MONITOR

RELATED APPLICATION

The current patent application is a non-provisional patent application and claims priority benefit, with regard to all common subject matter, of earlier-filed provisional patent applications: U.S. Application No. 61/753,747, titled "HEALTH AND WELLNESS MONITOR" and filed Jan. 17, 2013; and U.S. Application No. 61/868,880, titled "FITNESS MONITOR" and filed Aug. 22, 2013. The earlier-filed provisional patent applications are hereby incorporated into the current patent application in its entirety.

BACKGROUND

A fitness monitor is an electronic device that tracks the activity of a user, typically by sensing the motion of the user such as determining the number of steps taken by the user. Some fitness monitors may be worn on a user's wrist, arm, torso, leg, etc. Other fitness monitors may be carried or attached to clothing. Some fitness monitors include additional features such as presenting the time of day and communicating wirelessly with other electronic devices.

SUMMARY

Embodiments of the present technology provide a fitness monitor for tracking the activity levels of a user. The fitness monitor broadly comprises a housing, a wrist band, a motion sensor, a display, a non-transitory memory element, and a processing element. The wrist band is coupled to the housing and configured to attach to the user's wrist. The motion sensor is configured to sense motion of the user and generate motion data. The display is coupled to the housing and configured to present information associated with user activity. The memory element is located in the housing and configured to store the activity data and a daily activity goal. The processing element of the fitness monitor may determine, based on daily activity data, a daily activity goal corresponding to a predetermined level of activity for the user in a day, compute a level of inactivity corresponding to a mathematical difference between a current activity associated with the user in a first time period and a predetermined inactivity value. In embodiments, the processing element is operably coupled to the memory element and configured to determine, based on the activity data, daily activity data including a current number of steps taken by the user in a day, determine, based on the daily activity data, the daily activity goal corresponding to a predetermined number of steps to be taken by the user in a day, compute an activity countdown corresponding to a mathematical difference between the daily activity goal and the current number of steps taken by the user, compute a level of inactivity corresponding to a mathematical difference between the current number of steps taken by the user in a first time period and a predetermined inactivity value, and present, on the display, the activity countdown and inactivity indicia indicating the level of inactivity.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present technology will be apparent from the following detailed description of the embodiments and the accompanying drawing figures.

BRIEF DESCRIPTION OF THE DRAWING FIGURES

Embodiments of the present technology is described in detail below with reference to the attached drawing figures, wherein.

Figure 1:
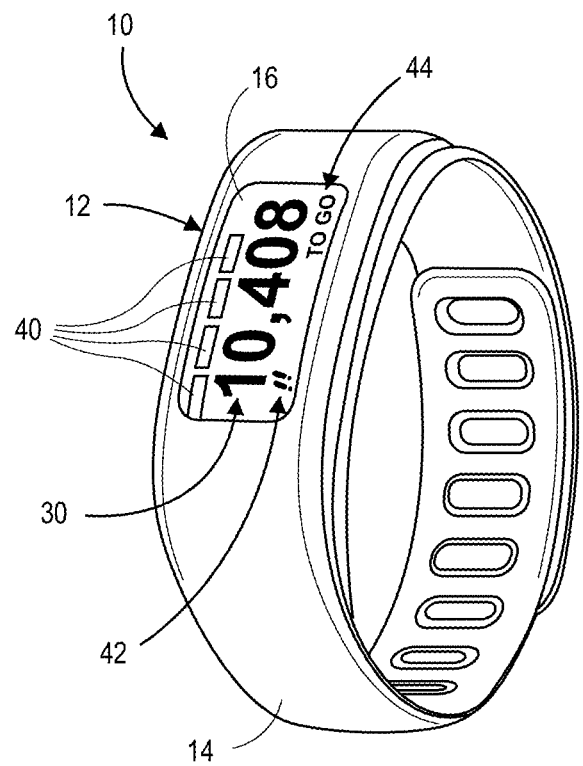
FIG. 1 is a front perspective view of a fitness monitor constructed in accordance with various embodiments of the present technology.

The drawing figures do not limit the present technology to the specific embodiments disclosed and described herein. The drawings are not necessarily to scale, emphasis instead being placed upon clearly illustrating the principles of the technology.

DETAILED DESCRIPTION

The following detailed description of the technology references the accompanying drawings that illustrate specific embodiments in which the technology can be practiced. The embodiments are intended to describe aspects of the technology in sufficient detail to enable those skilled in the art to practice the technology. Other embodiments can be utilized and changes can be made without departing from the scope of the present technology. The following detailed description is, therefore, not to be taken in a limiting sense. The scope of the present technology is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 2:
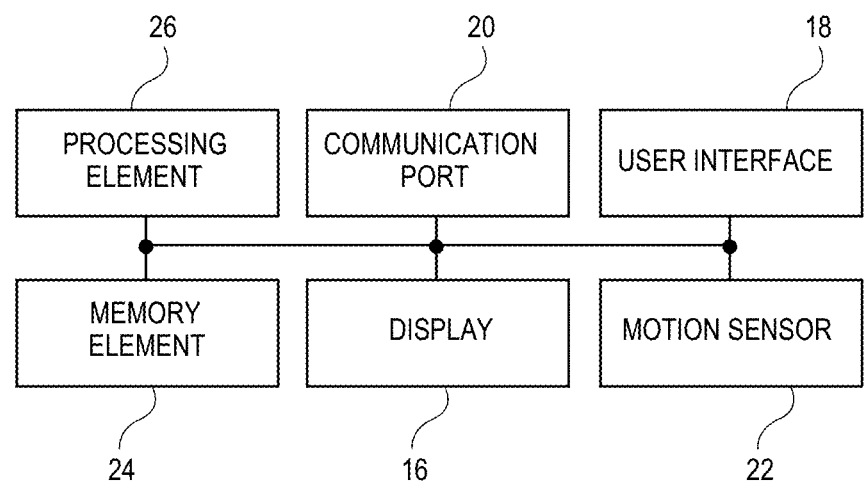
FIG. 2 is a schematic block diagram of components of the fitness monitor of FIG. 1.

Embodiments of the technology will now be described in more detail with reference to the drawing figures. Referring initially to FIGS. 1 and 2, a fitness monitor 10 is illustrated.

The fitness monitor 10 generally tracks the activity levels of a user in order to promote good health and fitness. The fitness monitor 10 broadly comprises a housing 12, a wristband 14, a display 16, a user interface 18, a communication port 20, a motion sensor 22, a memory element 24, and a processing element 24.

The housing 12, as seen in FIG. 1, generally houses at least a portion of the other components. In some embodiments, the housing 12 may include an upper portion and a lower portion that are coupled together with screws or other fasteners. The housing 12 may also include an inner chamber in which additional components such as batteries are located. In some embodiments, the housing 12 may be waterproof up to 50 meters of water depth.

The wristband 14, as seen in FIG. 1, generally allows the fitness monitor 10 to be worn on the wrist of the user. In embodiments, wristband 14 may be modified to secure fitness monitor 10 to other parts of the user's body (arm, torso, leg, ankle, etc.) or to the user's clothing (e.g., shirt, belt, shoe, etc.) as a clip. The wristband 14 may be formed from flexible, supple material such that the fitness monitor 10 can be worn by the user for long periods of time. The wristband 14 may include a plurality of holes and corresponding coupling mechanisms that allow the length of the wristband 14 to be adjusted. The wristband 14 may couple to opposing ends of the housing 12. When the wristband 14 is worn on a user's wrist, the fitness monitor 10 may resemble a wristwatch.

The display 16, as seen in FIGS. 1 and 3-7, generally presents information associated with the user's activity. For example, display 16 may present the user's daily activity goals and activity data. The display 16 may be formed from, or may include, the following technologies: plasma, light-emitting diode (LED), organic LED (OLED), Light Emitting Polymer (LEP) or Polymer LED (PLED), liquid crystal display (LCD), thin film transistor (TFT) LCD, electronic paper, electronic ink, and the like, or combinations thereof. The display 16 may be coupled to an upper or outer surface of the housing 12 and may receive information to be presented from the processing element 24.

The display 16 may present letters, numbers, words, icons, symbols, indicia, and the like. In various embodiments, the display 16 may display information such as the time of day 28, a current number of steps taken 30, an activity countdown 32 toward reaching a daily activity goal, a number of beyond-goal steps 34, a distance 36 walked or traveled, a number of calories 38 burned, and the like. To be clear, display 16 of fitness monitor 10 may present information associated with any physical activity. For example, motion sensor 22 of fitness monitor 10 may sense motion of the user wearing the fitness monitor 10 associated with swimming (e.g., number of strokes, length of strokes, etc.), skating (e.g., ice skating, inline skating, etc.), skiing, rowing, bicycling, aerobics, or any other physical activity.

Fitness monitor 10 may determine a heart rate for a user and determine user activity based on heart rate information. In embodiments, communication port 20 may receive data associated with a user's heart rate. The heart rate data may be received by processing element 26 to determine user activity, an activity count down 32 toward reaching a daily activity goal, and a number of calories 38 burned. Display 16 of fitness monitor 10 may be configured to present user activity information determined based on heart rate information associated with the user, motion sensed by motion sensor 22, or a combination thereof. Processing element 24 may also use the heart rate information to determine heart rate variability. Fitness monitor 10 may determine energy expenditure based on heart rate information, such as heart rate variability, and user-specific information, such as age, gender, weight, height and fitness class (i.e., overall physical fitness level).

Figure 8:
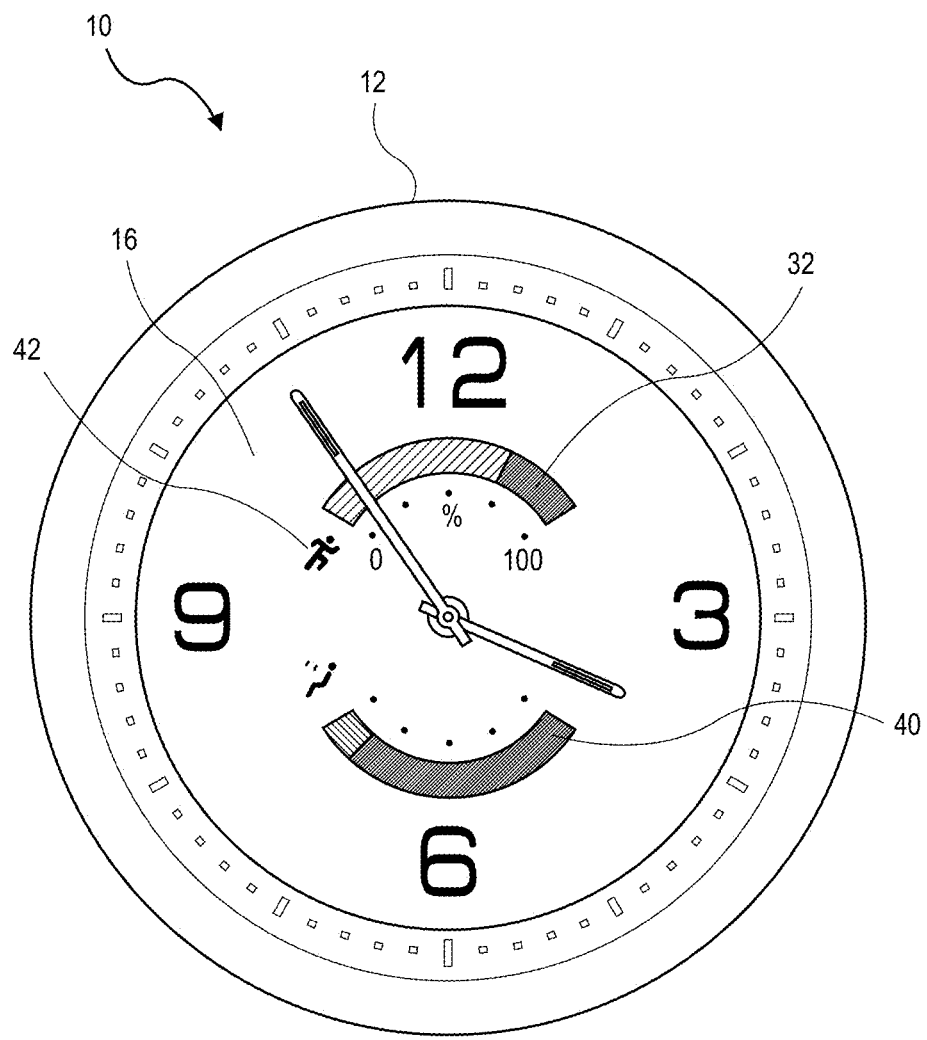
FIG. 8 is a front view of a fitness monitor constructed in accordance with various embodiments of the present technology.

The display 16 may present a status indicia accompanying the display of activity countdown 32 (e.g., a countdown indicia 44) and beyond-goal steps 34 (a positive indicia 46). In embodiments, a current number of steps taken 30 and an activity countdown 32 may include a numeric value presented on display 16 or a continuous element to indicate a current activity and status towards reaching a daily activity goal. The continuous element may use a single interrupted component or discrete components. For example, as shown in FIG. 8, fitness monitor 10 may include a housing 12 having a display 16 that depicts an activity countdown 32 that includes a continuous element to indicate a present status towards reaching a daily activity goal (e.g., user's activity levels are approximately 70% of a daily activity goal determined for the user). The fitness monitor 10 may also include a housing 12 having a display 16 that depicts an activity countdown 32 using discrete light emitting elements (e.g., LEDs) that are illuminated to indicate a status towards reaching a daily activity goal (e.g., user's activity levels of approximately 60% are indicated by illuminating 3 of 5 sequential LEDs). In embodiments, display 16 of fitness monitor 10 may present a current number of steps 30 taken in place or in combination with an activity countdown 32. For example, as shown in FIG. 8, display 16 may present a current number of steps taken 30 as a continuous element in place of an activity countdown 32. Content associated with an activity countdown 32 (e.g., indicating status in relation to a daily activity goal) is modified to communicate a current number of steps 30.

Fitness monitor 10 may present current activity level information (e.g., current number of steps taken 30, activity countdown 32, inactivity indicia 40, etc.) on display 16 using various colors to indicate the user's progress in addition to or in place of the presentation of the activity level information on display 16. The use of distinctive colors on display 16 enables a user to quickly ascertain his current performance levels (e.g., progress in satisfying daily activity goals, levels of inactivity, and other fitness information). In embodiments, display 16 may incorporate be operable to output information and backlighting in a plurality of colors. For example, a high level of inactivity may be indicated by presenting fitness information or backlighting using the color red (or a plurality of inactivity indicia 40) and a low level of inactivity may be indicated by presenting fitness information or backlighting using the color green (or presenting no inactivity indicia 40). Display 16 may provide an indication of current number of steps taken 30 or activity countdown 32 by presenting fitness information or backlighting using the color yellow. Display 16 may provide an indication of beyond-goal steps 34 by presenting fitness information or backlighting using the color green. Progress may be indicated by varying shades of a color associated with a certain activity level. For example, display 16 may use a light green color to present fitness information or backlight display 16 for a user that has a low number of beyond-goal steps 34 and a dark green color to present fitness information or backlight display 16 for a user that has a high number of beyond-goal steps 34.

In embodiments, a user may specify which activity level information (e.g., current number of steps taken 30, activity countdown 32, inactivity indicia 40, etc.) is to be conveyed using a plurality of colors on display 16 by inputting a selection using user interface 18. In embodiments, use of colored backlighting may enable reduction of information presented on display 16. For example, the user can choose to apply various colors to indicate inactivity indicia 40 on display 16 and use of numeric values to present a current number of steps taken 30. Numerous other combinations of display 16 presenting activity level information using a plurality of available colors are possible.

The display 16 may also show inactivity indicia 40 indicating varying levels of inactivity based on the number of indicia presented to the user. The inactivity indicia 40 may include a single inactivity indicia or a plurality of inactivity indicia that provides for a continuous or segmented presentation of indicating varying levels of inactivity. The display 16 may also present activity type indicia associated with the type of activity data used to determine an activity countdown 32 (or beyond-goal steps 34) and any inactivity indicia that may be presented on display 16. For example, a steps indicia 42, as shown in FIGS. 1 and 8, may accompany the display of current number of steps taken 30, a distance indicia 48 may accompany the display of distance 36 walked, a calories indicia 50 may accompany the display of number of calories 38 burned.

The user interface 18 generally allows the user to select which information is shown on the display 16 and may include one or more pushbuttons, or touch areas, such as a touchscreen. For example, the user may activate the user interface 18, such as by pushing a button, to cycle through a plurality of screens of data, wherein each screen of data may include informational items, such as those listed above. The user interface 18 may be located either on the housing 12, on the display 16, or on the wrist band 14.

The communication port 20 generally allows the user to upload data to, download data from, or adjust the settings of the fitness monitor 10. The communication port 20 may be wired or wireless and may include antennas, signal or data receiving circuits, and signal or data transmitting circuits. The communication port 20 may transmit and receive radio frequency (RF) signals and/or data and may operate utilizing communication standards such as ANT, ANT+, Bluetooth™ low energy (BLE), Near Field Communications (NFC), or the like. In various embodiments, the communication port 20 may transmit and receive data using the industrial, scientific, and medical (ISM) band at 2.4 gigahertz (GHz). Furthermore, in some embodiments, the communication port 20 may communicate with a wireless dongle that connects to the USB port of a desktop, laptop, notebook, or tablet computer, or other electronic device. An exemplary communication port 20 includes an nRF51922 RF integrated circuit (IC) from Nordic Semiconductor of Trondheim, Norway.

Fitness monitor 10 may include an input/output interface that may enable interaction between fitness monitor 10 and an external display, processing element, memory element and/or user interface associated with a secondary electronic device (e.g., associated with a smartphone, tablet, personal computer, etc.). In embodiments, an external display and user interface may be utilized by fitness monitor 10 to present fitness information provide and provide user interface functionality. Fitness device 10 may not include a display 16 and may utilize an external display to present fitness information and provide user interface functionality. Fitness device 10 may supplement the functionality of a display 16 and user interface included in fitness device 10 with an external display, processing element, memory element and/or user interface associated with the secondary electronic device. For example, fitness device 10 may user communication port 20 to transmit fitness data (unprocessed, semi-processed or fully processed) to enable a secondary electronic device to provide user interface and/or visual or audible output functionality (using a display or speaker associated with the secondary device), processing functionality (using a processing element associated with the secondary device) or data storage functionality (using a memory element associated with the secondary device). In embodiments, external components may be operable to perform any of the functionality associated with the display 16, user interface 18, memory element 24, motion sensor 22 or processing element 26 as described herein.

In embodiments, fitness device 10 may include a location determining component to determine a current location of the housing 12. The location determining component may include a global positioning system (GPS) receiver, a satellite navigation receiver (e.g., GLONASS), a cellular signal receiver, an RF triangulation processor, an enhanced positioning system such as real time kinematic (RTK), or combinations thereof. The location determining component may supply the current location of the housing 12 to processing element 26.

The motion sensor 22 generally senses motion of the fitness monitor 10 and, in turn, the user wearing fitness monitor 10 on a limb (e.g., wrist, arm, torso, leg, ankle, etc), carrying fitness monitor 10 or having fitness monitor 10 attached to clothing or accessories commonly stored on the user's body (e.g., keys, workplace security badge, etc.). The motion sensor 22 may include accelerometers, tilt sensors, inclinometers, gyroscopes, combinations thereof, or other devices including piezoelectric, piezoresistive, capacitive sensing, or micro electromechanical systems (MEMS) components. The motion sensor 22 may sense motion along one axis of motion or multiple axes of motion, such as the three orthogonal axes X, Y, and Z. An exemplary motion sensor 22 is the ADXL362 3-axis accelerometer from Analog Devices of Norwood, Mass. The motion sensor 22 generally communicates motion data to the processing element 24. The rate at which the motion sensor 22 communicates motion data may vary from approximately 50 hertz (Hz) to approximately 100 Hz.

The memory element 24 generally stores information regarding daily activity goals and activity data and may include non-transitory components such as read-only memory (ROM), programmable ROM, erasable programmable ROM, random-access memory (RAM), cache memory, and the like, or combinations thereof. The memory element 24 may store instructions, code, code segments, software, firmware, programs, applications, apps, services, daemons, or the like.

The processing element 24 generally determines levels of inactivity and whether daily activity goals are met. The processing element 24 may include processors, microprocessors, microcontrollers, digital signal processors (DSPs), field-programmable gate arrays (FPGAs), analog and/or digital application-specific integrated circuits (ASICs), or the like, or combinations thereof. An exemplary processing element 24 includes a 32-bit Cortex M0 processor, licensed by ARM Holdings of Cambridge, England. In various embodiments, the Cortex M0 processor is packaged with the nRF51922 RFIC of the communication port 20. The processing element 24 may further include or be in communication with oscillators or periodic signal generators from which the time of day can be derived. The processing element 24 may generally execute, process, or run instructions, code, code segments, software, firmware, programs, applications, apps, processes, services, daemons, or the like, or may step through states of a finite-state machine. The processing element 24 may be in communication with the memory element 24 through address busses, data busses, control lines, and the like. Furthermore, the processing element 24 may send data to the display 16, may receive data from the motion sensor 22 and the user interface 18, and may send and receive data from the communication port 20.

Figure 5:
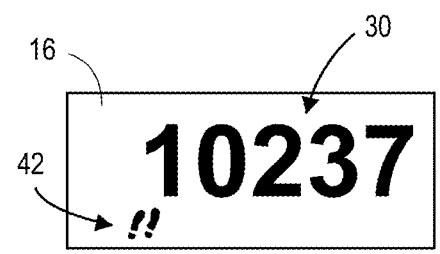
FIG. 5 shows the display of the fitness monitor of FIG. 1, illustrating a current number of steps taken.

The processing element 24 may be configured or programmed to perform the following functions. The processing element 24 may receive motion data from the motion sensor 22 and may process the motion data to determine activity data. In various embodiments, the activity data may include the current number of steps taken 30 by the user, distance 36 walked or traveled, number of calories 38 burned, or a combination thereof. The activity data may also include other types of movements that may be identified from motion data provided by motion sensor 22. The processing element 24 may process the available motion data to determine the total number of steps that have been taken by the user over a given time period. For example, the processing element 24 may determine the total number of steps that have been taken by the user for each 24-hour period (i.e., a single day). It is to be clear that the period of time analyzed to determine activity data may be any period (e.g., 15 minutes, hourly, 6 hours, daily, weekly, monthly, etc.). In embodiments, the period of time used to analyze activity data may be inputted to fitness monitor 10 by the user using user interface 18, based on the user's historical activity data, a training plan stored in memory element 24 or a user profile. Memory element 24 may store activity data for extended periods that exceed the given time period to provide historical activity data and identify changes in the activity data over an extended period of time (e.g., historically increasing trend in stored activity data, historically decreasing trend in stored activity data, etc.). The processing element 24 may communicate the current number of steps taken 30 to the display 16 for presentation to the user as shown in FIG. 5.

The fitness monitor 10 may initially store a daily activity goal that corresponds to a predetermined number of steps to be taken by the user in a given time period (e.g., one day). In certain embodiments, activity goals of other time periods, such as hourly or a week, could be provided as well. In embodiments, given the daily activity goal in terms of a total number of steps to be taken in a day and the current number of steps taken 30 by the user, the processing element 24 may determine the activity countdown 32, which is the mathematical difference between the daily activity goal and the current number of steps taken 30. The activity countdown 32 represents the number of steps remaining to be taken for the user to reach the daily activity goal. The processing element 24 may update the activity countdown 32 by subtracting a step (decrementing) from the activity countdown 32 for each step that is taken by the user as determined from the motion data from the motion sensor 22.

Figure 3A:
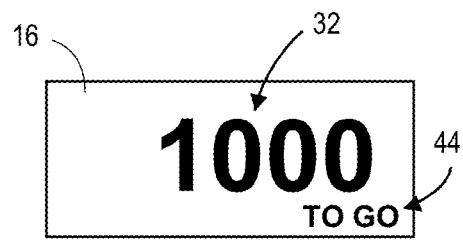
FIG. 3A shows a display of the fitness monitor of FIG. 1, illustrating a first number of steps of an activity countdown.
Figure 3B:
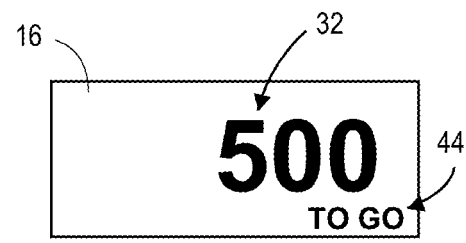
FIG. 3B shows a display of the fitness monitor of FIG. 1, illustrating a second number of steps of the activity countdown.
Figure 3C:
FIG. 3C shows a display of the fitness monitor of FIG. 1, illustrating a third number of steps of the activity countdown.
Figure 3D:
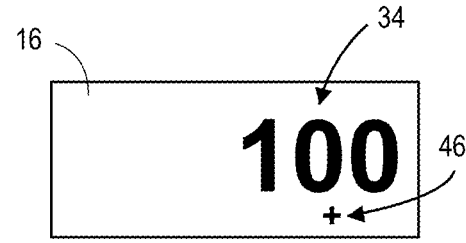
FIG. 3D shows a display of the fitness monitor of FIG. 1, illustrating a first number of beyond-goal steps.

As depicted in FIGS. 3A and 3B, display 16 may present countdown indicia 44 and an activity countdown 32 that is decreased from 1000 units of the activity data to 500 units of the activity data (e.g., reduce the steps to reach the daily activity goal from 1000 steps to 500 steps). In embodiments monitoring steps taken by the user, the activity countdown 32 equals zero when the current number of steps taken 30 equals the daily activity goal, as shown on the display 16 depicted in FIG. 3C, and, when the current number of steps taken 30 exceeds the daily activity goal, the processing element 24 may communicate to the display 16 the number of beyond-goal steps 34 which represents the steps that exceed the daily activity goal, as shown on the display 16 depicted in FIG. 3D. When the display 16 is showing the number of beyond-goal steps 34, the processing element 24 may add a step to the number of beyond-goal steps 34 for every step that is taken in excess of the daily activity goal. A transition from the display of an activity countdown 32 to beyond-goal steps 34 may be accompanied by a change in a status indicia presented on the display. For instance, as shown in FIGS. 3A-3D, status indicia of a countdown indicia 44 accompanying the display of activity countdown 32, which may be presented when the current number of steps taken by the user is less than the predetermined number of steps to be taken by the user, may be replaced with status indicia of a positive indicia 46 accompanying the display of number of beyond-goal steps 34 when the current number of steps taken by the user exceeds the predetermined number of steps to be taken by the user. The activity countdown 32 may be shown on the display 16 if the user selects it using the user interface 18. In addition, the processing element 24 may communicate to the display 16 to automatically switch from the activity countdown 32 to the number of beyond-goal steps 34 when the current number of steps taken 30 exceeds the daily activity goal. In embodiments, display 16 may communicate the number of beyond goal steps 34 with a continuous element. For example, as shown in FIG. 8, display 16 may present a number of beyond goal steps 34 as a continuous element in place of an activity countdown 32. Content associated with an activity countdown 32 (e.g., indicating status in relation to a daily activity goal) is modified to communicate a number of beyond goal steps 34.

The processing element 24 may store daily activity data, such as the current number of steps taken 30, in the memory element 24 at the end of each given time period as a total number of steps taken for that period (e.g., each day). At the end of each given time period, the processing element 24 may also reset the current number of steps taken 30 to zero so that the first step taken by the user in the following period is step number 1 (e.g., the 24-hour period if tracking each day).

The processing element 24 may further adjust the daily activity goal for each day based on the daily activity data, such as the history of the total number of steps taken, and the extent to which the user has exceeded daily activity goals in the past. In embodiments, fitness monitor 10 may propose a daily activity goal to the user, who may accept or modify the proposal, or enable input of a daily activity goal by the user. For example, a user may accept a proposed daily activity goal that is higher than the daily activity goal for the previous day or modify by the proposed daily activity goal based on the user's training preferences and goals.

Fitness monitor 10 may be configured to determine daily activity goals and predetermined inactivity values based on a user selection of a training level. In embodiments, low, medium and high training levels may be used by processing element 24 to determine daily activity goals and predetermined inactivity values. For instance, selection of the low training level may result in processing element 24 determining daily activity goals and predetermined inactivity values that increment at a rate that is lower than the medium and high training levels in order to encourage the user to increase his activity levels and reduce inactivity levels at a comfortable rate. Selection of the high training level may result in processing element 24 determining daily activity goals and predetermined inactivity values that increment at a rate that is higher than the low and medium training levels in order to encourage the user to maximize his activity levels and minimize inactivity levels over a period of use.

In various embodiments, the processing element 24 may perform a mathematical operation of the total number of steps taken for a period of time to determine the daily activity goal. For example, each day, the processing element 24 may perform a moving or windowed average on the total number of steps that were recorded for a number of 24-hour periods or calendar days before that day. The daily activity goal may be the average number of steps calculated for all stored activity data or a subset thereof. Alternatively, the processing element 24 may perform other statistical functions on the total number of steps taken for a number of days, such as the median, the highest value, the lowest value, and the like, when determining the daily activity goal for a given day. Activity data stored in memory element 24 may be prior activity data of the user, a third person, or computer-generated simulation data (e.g., theoretical profile). Visual and/or audible feedback information may be provided on the user to communicate the user's current status and accomplishments of daily activity goals (e.g., graphic presented on display 16).

In embodiments, fitness monitor 10 may analyze the user's historical activity data to determine a daily activity goal that encourages users to gradually increase the daily activity goal over time to improve the user's physical performance. In embodiments, processing element 26 of fitness monitor 10 may evaluate the user's historical activity data and then apply a stored training plan or an adaptive dynamic system to determine a daily activity goal for that user. In embodiments, processing element 26 may take the extent the user has exceeded daily activity goals into consideration when determining new daily activity goals. For example, daily activity goals may be increased more aggressively for users that are substantially exceeding recent daily activity goals in order to challenge the user.

Fitness monitor 10 may intelligently raise the daily activity goal from an initial daily activity goal to a significantly higher daily activity goal over a series of intermediate increases based on stored activity data that may be associated with the user or based on a user profile (e.g., increasing the daily activity from the 50th percentile of stored activity data to a double the stored daily activity goals). Processing element 26 of fitness monitor 10 may apply a stored training plan to determine an initial daily activity goal based on stored activity data (e.g., total number of steps taken) for a plurality of time periods and then adjust the daily activity goal by a pre-determined amount each day to a significantly higher daily activity goal. For example, processing element 26 may use stored activity data to initially determine a daily activity goal that is the median (50th percentile) of stored activity data (e.g., total number of steps taken) for a plurality of time periods and then increase the daily activity goal by 2% until peak user performance is satisfied. In embodiments, processing element 26 may apply a user profile to determine an initial activity goal based on the user's health characteristics (e.g., age, weight, healthiness, etc.) and then increase the daily activity goal to a significantly higher daily activity goal. In embodiments, the daily activity goal may be based on activity data corresponding to a particular day of the week stored in memory element 24. Fitness monitor 10 may account for trends in the user's activity levels to identify days of the week during which activity levels may be improved more easily than other days of the week. For instance, processing element 26 may access all, or a predetermined number of, stored activity data in memory element 24 for the current day to determine a daily activity goal for the current day (i.e., evaluate stored activity data for recent Wednesdays to determine the daily activity goal for this Wednesday). Processing element 26 may compute a simple average or median of all stored activity data for a relevant day of the week to determine a daily activity goal and/or apply weighting to more recently stored activity data associated with a day of the week. For example, additional weight may be applied to more recent activity data for a day of the week (i.e., same day last week) to improve user performance.

Processing element 26 of fitness monitor 10 may also apply an adaptive dynamic system that determines an initial daily activity goal and subsequent modifications to said daily activity goal based on the user's training preferences and goals (e.g., increase user activity, maintain user activity, etc.). For example, for users desiring to aggressively increase user activity, processing element 26 may initially determine the 75th percentile of stored activity data for a plurality of time periods and then variably increase the daily activity goal by percentages (e.g., 5-20%) that will comply with the user's training preferences and goals.

Memory element 24 of fitness monitor 10 may store a plurality of training plans available for use in determining daily activity goals. For example, memory element 24 may store ten training plans ranging from least to most challenging that may be selected for determining a daily activity goal. The least challenging training plan may determine daily activity goals that are intelligently raised from the 25th percentile of stored activity data to 75th percentile over a series of intermediate increases. The most challenging training plan may determine daily activity goals that are intelligently raised from the 75th percentile of stored activity data to three times the maximum stored activity data over a series of intermediate increases.

In embodiments, a stored training plan may be selected for use by a user (inputted using user interface 18) or automatically identified by the fitness monitor 10 based on user activity data. For example, processing element 26 pay identify a stored training plan for use by applying curve fitting of the user's stored activity data to data associated with stored training plans in order to identify the training plan that meets the user's current performance levels, training preferences and performance goals.

In embodiments, a user may transmit activity data stored in memory element 24 of fitness monitor 10 using communication port 20 to an online community (e.g., social website) accessible via the Internet. Other users may share their activity data for comparison and challenge purposes (e.g., activity data associated with user profiles). For example, a user may load the activity data of another user to memory element 24 for use by processing element 26 to determine daily activity goals, predetermined inactivity values, and other fitness information. In embodiments, activity data may be shared amongst users to determine the activity levels of each user relative to others within the online community (e.g., comparison to group leader, group average, etc.).

The processing element 24 may also monitor the current activity data to determine a level of inactivity. If the current number of steps taken 30 for a predetermined period of time is below a predetermined inactivity value (e.g., 25 steps per hour), then the processing element 24 may alert the user that he has been inactive by communicating with the display 16 to show at least one inactivity indicia 40, as seen in FIG. 1. In some embodiments, the period of time and the inactivity value of the number of steps may be set by the manufacturer of the fitness monitor 10, automatically determined by the fitness monitor 10, or adjusted by user inputs to user interface 18. Furthermore, the processing element 24 may communicate with the display 16 to show one inactivity indicia 40 for each period of time that the current number of steps taken 30 is below the inactivity value. For example, the processing element 24 may communicate with the display 16 to show one inactivity indicia 40 for each hour that the current number of steps taken 30 is below the predetermined inactivity value. For example, if the current number of steps taken 30 is below the inactivity value for three hours, then three inactivity indicia 40 may be shown on the display 16.

In embodiments, processing element 24 may compute a level of inactivity corresponding to a mathematical difference between the current activity associated with the user in a first time period and a predetermined inactivity value. In embodiments, processing element 24 may then processing element 24 may communicate with the display 16 to increase the inactivity indicia for each first time period the current activity is less than the predetermined inactivity value and communicate with the display 16 to decrease the inactivity indicia presented on the display for each second time period of increased levels of activity data.

As described above, the inactivity indicia 40 may indicate varying levels of inactivity using a single inactivity indicia or a plurality of inactivity indicia to provide in a continuous or segmented manner. For example, as shown in FIG. 1, the inactivity indicia 40 presented on display 16 may include four segmented elements (e.g., one segmented element is presented to communicate a low level of inactivity and all four segmented elements are presented to communicate the highest level of inactivity). In other embodiments, the inactivity indicia 40 presented on display 16 may include be continuous element that is filled to reflect varying levels of inactivity (e.g., 25% of a presented continuous element is filled to communicate a low level of inactivity and 100% of the continuous element is filled to communicate the highest level of inactivity). For example, as shown in FIG. 8, fitness monitor 10 may include a housing 12 having a display 16 that depicts inactivity indicia 40 that includes a continuous element to indicate varying levels of inactivity (e.g., increasing towards a first level of inactivity).

As the user resumes his activity, the processing element 24 may monitor the current activity data and may communicate with the display 16 to remove one or more inactivity indicia 40 currently presented on display 16 based on the current number of steps taken 30 or the time period during which activity (e.g., walking) is detected based on motion data from the motion sensor 22. For example, if the processing element 24 detects that the current number of steps taken 30 for a predetermined period of time is above a predetermined inactivity value (e.g., the user has taken more than 25 steps in the last hour), then the processing element 24 may communicate with the display 16 to remove one inactivity indicia 40 that is currently presented to the user. Furthermore, the processing element 24 may communicate with the display 16 to remove one additional inactivity indicia 40 for predetermined period of time is above a predetermined inactivity value.

Figure 6:
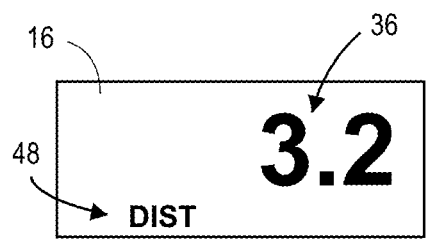
FIG. 6 shows the display of the fitness monitor of FIG. 1, illustrating a distance walked by a user.
Figure 7:
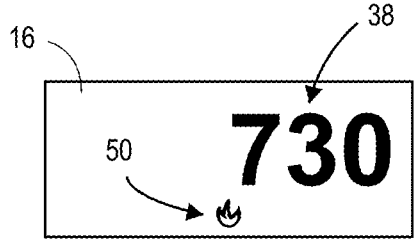
FIG. 7 shows the display of the fitness monitor of FIG. 1, illustrating a number of calories burned by the user.

The processing element 24 may also utilize data input from the user regarding the user's height or length of stride to determine the distance 36 walked by the user, as shown on the display 16 depicted in FIG. 6. The user may input personal data using user interface 18. In addition, the processing element 24 may utilize data input from the user regarding the user's weight to determine the number of calories 38 burned, as shown on the display 16 depicted in FIG. 7. As described above, the daily activity goal presented on display 16 may also be based on distance 36 walked or traveled, number of calories 38 burned, or a combination thereof.

The fitness monitor 10 may operate as follows. Accompanying the fitness monitor 10 may be a software program or application that allows the user to input personal data, such as the user's height, weight, gender, age, and the like, which is relevant to setting activity goals. Prior to usage of the fitness monitor 10, the user may utilize an external electronic device, such as a computer, a tablet, or a smart phone, that is executing the program or application to enter the personal data. The user may then download the data to the fitness monitor 10 through the communication port 20. In addition, the fitness monitor 10 may receive an initial setting of the time of day from the electronic device.

Figure 4:
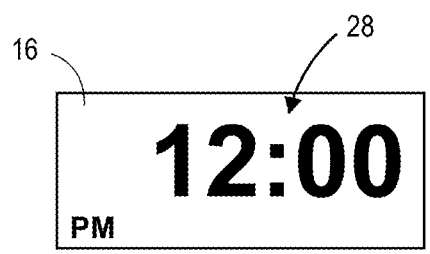
FIG. 4 shows the display of the fitness monitor of FIG. 1, illustrating the time of day.

The display 16 may show the time of day by default, as seen in FIG. 4. The user may activate the user interface 18, such as by pressing a button, to change the information shown on the display 16. For example, as seen in FIGS. 3-7, the display 16 may cycle through the following information: the time of day 28, the activity countdown 32, the current number of steps taken 30, the number of beyond-goal steps 34, the distance 36 walked, and the number of calories 38 burned. The display 16 may also show indicia that accompanies each item of information. Furthermore, the display 16 may show one or more inactivity indicia 40, if appropriate, as seen in FIG. 1.

The fitness monitor 10 may continuously sense motion of the user, through the motion sensor 22, while it is being worn by the user on a limb (e.g., wrist, arm, torso, leg, etc), carried, or attached to clothing. The processing element 24, receiving data from the motion sensor 22, may determine activity data including the current number of steps taken 30. The user may check on his progress toward the daily activity goal at any time by activating the user interface 18 to view the current number of steps taken 30, the activity countdown 32, or the number of beyond-goal steps 34 if the current number of steps taken 30 has exceeded the daily activity goal.

In embodiments that the fitness monitor 10 determines activity goals based on steps taken by the user for each day, the fitness monitor 10 may track the total number of steps that the user takes each day and intelligently adjust the daily activity goal accordingly. Thus, users whose total number of steps is increasing over time may continue to improve their physical performance, while other users may be presented with more easily attainable goals. Using a statistical analysis, as discussed above, the processing element 24 may increase the daily activity goal if the user's total number of steps taken per day is trending generally upward or decrease the daily activity goal if the user's total number of steps taken per day is trending generally downward.

The fitness monitor 10 may also track the activity data to alert the user to periods of inactivity. Visual and/or audible feedback information may be provided on the user to communicate the user's period of inactivity (e.g., graphic presented on display 16). If the user has been sitting (i.e., mostly sedentary) for a long period of time, then the number of steps taken for that period is likely to be less than the inactivity value. For each period of time that the number of steps taken is less than the inactivity value, the display 16 may show an additional inactivity indicia 40. When the user views the inactivity indicia 40 presented on display 16, he may resume physical activity, such as walking, again. If the user walks continuously for a predetermined second time period of increased levels of activity data, such as one minute or hour, then an inactivity indicia 40 may be removed from the display 16. In embodiments For example, The processing element 26 may determine levels of inactivity corresponding to low levels of activity data for a first time period and levels of activity corresponding to higher levels of activity data for a second time period. The fitness device 10 may present indicia indicating inactivity when levels of activity data do not meet a predetermined inactivity value (e.g., 25 steps per first time period) and remove any indicia of indicating inactivity when levels of activity data meet or surpass a predetermined inactivity value. The first time period and second time period may be equal (e.g., 15 minutes for both) or different (e.g., 15 minutes for the first time period and 2 minutes for the second time period). For example, the second time period may be a shorter length of time than the first time period. This may provides for increased levels of activity over a plurality of second time periods to remove multiple inactivity indicia 40 presented on display 16 over the first time period. For instance, one of a plurality of inactivity indicia 40 presented on display 16 as a result of inactivity levels determined over 15 minute intervals may be sequentially removed for each 2-minute period of increased activity levels (e.g., user takes more than 25 steps). In embodiments, the display 16 of fitness device 10 may present a daily activity goal and a plurality of inactivity indicia enabling a user to determine a present activity level in relation to a desired goal and an indication of recent inactivity. The presentation of information associated with the user's activity may motivate a user to embrace or sustain a healthy lifestyle.

Although the technology has been described with reference to the embodiments illustrated in the attached drawing figures, it is noted that equivalents may be employed and substitutions made herein without departing from the scope of the technology as recited in the claims.

Having thus described various embodiments of the technology, what is claimed as new and desired to be protected by Letters Patent includes the following:

What is claimed is:

1. A fitness monitor comprising:
a housing;
a wrist band coupled to the housing and configured to attach to a wrist of a user;
a motion sensor configured to sense motion of the user and generate motion data;
a display coupled to the housing and configured to present information associated with user activity;
a non-transitory memory element located in the housing and configured to store activity data and a daily activity goal; and
a processing element located in the housing and operably coupled to the memory element, the processing element configured to:
determine, based on the activity data, daily activity data including a current number of steps taken by the user in a day,
determine, based on the daily activity data, the daily activity goal corresponding to a predetermined number of steps to be taken by the user in a day,
compute an activity countdown corresponding to a mathematical difference between the daily activity goal and the current number of steps taken by the user,
compute a level of inactivity corresponding to a mathematical difference between the current number of steps taken by the user in a first time period and a predetermined inactivity value, and
present, on the display, the activity countdown and inactivity indicia indicating the level of inactivity.

2. The fitness monitor of claim 1, wherein the processing element is further configured to increase the daily activity goal based on historically increasing daily activity data and decrease the daily activity goal based on historically decreasing daily activity data.

3. The fitness monitor of claim 1, wherein the inactivity indicia includes a plurality of inactivity indicia indicating varying levels of inactivity and the processing element is further configured to communicate with the display to remove one inactivity indicia from the display for each second time period of increased levels of activity data.

4. The fitness monitor of claim 3, wherein the second time period is a shorter length of time than the first time period.

5. The fitness monitor of claim 1, wherein the activity data further includes a distance walked by the user and/or a number of calories burned by the user in a day.

6. The fitness monitor of claim 1, wherein the processing element is further configured to:
compute a number of beyond-goal steps when the current number of steps taken exceeds the daily activity goal, and
present, on the display, the number of beyond-goal steps.

7. The fitness monitor of claim 6, wherein a transition from the display of an activity countdown to beyond-goal steps may be accompanied by a change in a status indicia presented on the display.

8. The fitness monitor of claim 6, wherein an activity type indicia associated with a type of activity data used to compute the activity countdown or beyond-goal steps is presented on the display, the activity type indicia is one of a steps indicia, a distance indicia or a calories indicia.

9. The fitness monitor of claim 1, wherein the non-transitory memory element further stores training plans that are used by the processing element to determine the daily activity goal.

10. A fitness monitor comprising:
a housing;
a wrist band coupled to the housing and configured to attach to a wrist of a user;
a motion sensor configured to sense motion of the user and generate motion data;
a display coupled to the housing and configured to present information associated with the user activity;
a non-transitory memory element located in the housing and configured to store activity data and a daily activity goal; and
a processing element located in the housing and operably coupled to the memory element, the processing element configured to:
determine, based on the activity data, daily activity data including a current number of steps taken by the user in a day,
determine, based on the daily activity data, the daily activity goal corresponding to a predetermined number of steps to be taken by the user in a day,
increase the daily activity goal based on historically increasing daily activity data,
decrease the daily activity goal based on historically decreasing daily activity data,
compute a level of inactivity corresponding to a mathematical difference between the current number of steps taken by the user in a first time period and a predetermined inactivity value, and
present, on the display, an activity countdown based on the daily activity goal and inactivity indicia indicating the level of inactivity.

11. The fitness monitor of claim 10, wherein the inactivity indicia includes a plurality of inactivity indicia indicating varying levels of inactivity and the processing element is further configured to communicate with the display to present one inactivity indicia for each first time period of low levels of activity data.

12. The fitness monitor of claim 11, wherein the processing element is further configured to communicate with the display to remove one inactivity indicia from the display for each second time period of increased levels of activity data.

13. The fitness monitor of claim 10, wherein the activity data further includes a distance walked by the user and/or a number of calories burned by the user in a day and an activity type indicia associated with a type of activity data used to compute the activity countdown or beyond-goal steps is presented on the display, the activity type indicia is one of a steps indicia, a distance indicia or a calories indicia.

14. The fitness monitor of claim 13, wherein the processing element is further configured to:

compute a number of beyond-goal steps when the current number of steps taken exceeds the daily activity goal, and present, on the display, the number of beyond-goal steps.

15. The fitness monitor of claim 14, wherein a transition from the display of an activity countdown to beyond-goal steps may be accompanied by a change in a status indicia presented on the display.

16. A fitness monitor comprising:

a housing;

a wrist band coupled to the housing and configured to attach to a wrist of a user;

a motion sensor configured to sense motion of the user and generate motion data;

a display coupled to the housing and configured to present information associated with the user activity and inactivity indicia indicating varying levels of inactivity;

a non-transitory memory element located in the housing and configured to store activity data a daily activity goal; and a processing element located in the housing and operably coupled to the memory element, the processing element configured to:

determine, based on the activity data, daily activity data, determine, based on the daily activity data, the daily activity goal corresponding to a predetermined level of activity for the user in a day, compute a level of inactivity corresponding to a mathematical difference between the current activity associated with the user in a first time period and a predetermined inactivity value, communicate with the display to increase the inactivity indicia for each first time period the current activity is less than the predetermined inactivity value, and communicate with the display to decrease the inactivity indicia presented on the display for each second time period of increased levels of activity data.

17. The fitness monitor of claim 16, wherein the processing element is further configured to compute an activity countdown corresponding to a mathematical difference between the daily activity goal and the current activity associated with the user.

18. The fitness monitor of claim 17, wherein the processing element is further configured to:

compute a number of beyond-goal steps when the current number of steps taken exceeds the daily activity goal, and present, on the display, the number of beyond-goal steps.

19. The fitness monitor of claim 18, wherein the activity data further includes a distance walked by the user and/or a number of calories burned by the user in a day and an activity type indicia associated with a type of activity data used to compute the activity countdown or beyond-goal steps is presented on the display, the activity type indicia is one of a steps indicia, a distance indicia or a calories indicia.

20. The fitness monitor of claim 16, wherein the inactivity indicia includes a plurality of inactivity indicia to indicate the varying levels of inactivity and the processing element is further configured to increase the daily activity goal based on historically increasing daily activity data and decrease the daily activity goal based on historically decreasing daily activity data.

* * * * *